United States Patent [19]

Sunkara et al.

[11] Patent Number: 5,063,238
[45] Date of Patent: Nov. 5, 1991

[54] PREVENTION OF GLYCOPROTEIN ENVELOPED VIRUS INFECTIVITY BY PYRIDINYLOXAZOLE-2-ONES

[75] Inventors: Sai P. Sunkara; Winton D. Jones, both of Cincinnati, Ohio

[73] Assignee: Merrell Dow Pharmaceuticals Inc., Cincinnati, Ohio

[21] Appl. No.: 590,522

[22] Filed: Oct. 3, 1990

Related U.S. Application Data

[63] Continuation-in-part of Ser. No. 436,264, Nov. 13, 1989, abandoned.

[51] Int. Cl.$^5$ .............................................. A61K 31/44
[52] U.S. Cl. .................................... 514/340; 514/341
[58] Field of Search ................................. 514/340, 341

[56] References Cited

U.S. PATENT DOCUMENTS 4,698,353 10/1987 Schnettlev et al. ................. 514/340

Primary Examiner—Jerome D. Goldberg
Attorney, Agent, or Firm—Stephen L. Nesbitt

[57] ABSTRACT

This invention relates to pyridinyloxazole-2-ones which are useful anti-enveloped virus agents by virtue of their ability to act as protein kinase C inhibitors. These derivatives are disclosed to be effective in treating enveloped virus infections including HIV infections and are thus useful in the treatment of AIDS and ARC.

10 Claims, No Drawings

PREVENTION OF GLYCOPROTEIN ENVELOPED VIRUS INFECTIVITY BY PYRIDINYLOXAZOLE-2-ONES

This is a continuation-in-part of application Ser. No. 07/436,264, filed Nov. 13, 1989 now abandoned.

This invention relates to the use of certain pyridinyloxazole-2-ones in the treatment and prevention of infections by enveloped virus including retroviral, e.g., HIV, infections.

BACKGROUND OF THE INVENTION

A great deal of research is currently underway to develop treatments and cures for viral infections in humans and in animals. Notably the incidence of AIDS and ARC in humans is increasing at an alarming rate. The five year survival rate for those with AIDS is dispiriting and AIDS patients, whose immune systems have been seriously impaired by the infection, suffer from numerous opportunistic infections including Kaposi's sarcoma and *Pneumocystis carninii* pneumonia. No cure is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then randomly incorporated into the chromasomal DNA of the host cell making possible viral replication by later translation of the integrated DNA containing the viral genome.

Many of the known retroviruses are oncogenic or tumor causing. Indeed the first two human retroviruses discovered, denoted human T-cell leukemia virus I and II or HTLV-I and II, were found to cause rare leukemias in humans after infection of T-lymphocytes. The third such human virus to be discovered, HTLV-III, now referred to as HIV, was found to cause cell death after infection of T-lymphocytes, specifically the CD4+ subpopulation, and has been identified as the causative agent of acquired immune deficiency syndrome (AIDS) and AIDS related complex (ARC).

Retroviruses have, in addition to the usual viral capsid, an outer membrane of lipid and glycoprotein, similar to the membrane of ordinary cells. Indeed the lipid of the retroviral membrane is probably derived directly from the membrane of a previously infected host cell, however, the glycoprotein of the viral membrane is unique to the virus itself and is coded for by the viral genome. Infection of a host cell by a retrovirus initially relies on the interaction of various receptors on the host cell surface with the glycoprotein membrane envelope of the virus. Subsequently the virus and cell membranes fuse and the virion contents are released into the host cell cytoplasm. The glycoprotein envelope of the retroviruses plays an important role in both the initial interaction of the virion and the host cell and in the later fusion of the viral and host cell membranes.

In addition to the retroviruses, certain other viruses are coated or enveloped by a glycoprotein layer as well. Such viruses include the herpes simplex viruses (HSV), the influenza viruses, cytomegloviruses (CMG), and others.

Infection of human CD4+ cells by HIV has been shown to involve binding of the HIV gp120 surface protein to a receptor on the surface of the CD4+ cells, the CD4 receptor. Recently it has been observed that binding of HIV to CD4+ cells is accompanied by phosphorylation of CD4 and it has been suggested that this phosphorylation may be protein kinase C (PKC) mediated. Fields, et al., Nature, Vol. 333, 19 May 1988. Experiments indicate that the presence of the PKC inhibitor, 1,5-isoquinolinesulphonyl-2-methylpiperazine dihydrochloride, does not interfere with HIV cell surface binding but causes an accumulation of virus particles at the cell surface and inhibition of viral infectivity, thus supporting the concept that phosphorylation, subsequent to binding, is necessary for infectivity. Applicants have discovered that PKC mediated phospharglation is important in infectivity of Moloney Murine Leukemia virus (MoLV) as well, and applicants suggest that PKC mediated phosphorylation is an important step in host binding infectivity of enveloped viruses in general.

Applicants have determined that certain pyridinyloxazole-2-ones having PKC inhibiting activity are useful in the treatment of various enveloped virus infections including in the treatment of AIDS and ARC resulting from infection by HIV or other retroviruses.

SUMMARY OF THE INVENTION

The present invention is directed to certain pyridinyloxazole-2-ones of the formula

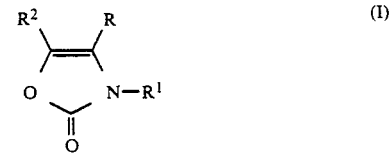

wherein

R and R₁ are each independently selected from the group consisting of hydrogen, $C_1$–$C_6$ alkyl, and phenyl or $C_1$–$C_3$ alkylphenyl wherein the phenyl ring is optionally substituted with one, two or three of the substituents selected from the group consisting of fluorine, chlorine, bromine, $C_1$–$C_4$ alkyl, and $C_1$–$C_4$ alkoxy;

R₂ is a 2-, 3-, or 4-pyridyl group wherein the pyridyl group is optionally substituted with one or two substituents selected from the group consisting of fluorine, chlorine, bromine, $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, cyano, carboxy, carb($C_1$–$C_5$)alkoxy, carbamido, ($C_1$–$C_5$)alkanoylamino, imidazolyl, nitro and trifluoromethyl or wherein the pyridyl group is optionally substituted with a phenyl group which is optionally substituted with one, two or three of the substituents selected from the group consisting of fluorine, chlorine, bromine, $C_1$–$C_4$ alkyl, and $C_1$–$C_4$ alkoxy; and to the pharmaceutically acceptable salts thereof.

DETAILED DESCRIPTION OF THE INVENTION

This invention concerns the use of the compounds of Formula I as agents effective in the treatment of infections of enveloped viruses.

As used herein, the terms "$C_1$–$C_3$ alkyl", "$C_1$–$C_4$ alkyl" and "$C_1$–$C_6$ alkyl" mean straight or branched chain alkyl groups having from one to three, from one to four, or from one to six carbon atoms respectively, and include such groups as methyl, ethyl, n-propyl, isopropyl, n-butyl, isobutyl, sec-butyl, tert-butyl, and the like, as well as vinyl, allyl, propynyl, butenyl, butadienyl, isopropenyl, and the like. The term "$C_1$-$C_4$ alkoxy" means alkoxy groups having from one to four carbon atoms, and includes such groups as methoxy, ethoxy, n-propoxy, isopropoxy, n-butoxy, isobutoxy, sec-butoxy, tert-butoxy, and the like. When R or $R_1$ is "optionally substituted phenyl or $C_1$-$C_3$ alkylphenyl", the one, two or three substituent(s) can be located at any available position on the phenyl ring.

The expression "a pharmaceutically acceptable acid addition salt" is intended to apply to any non-toxic organic or inorganic acid addition salt of the base compounds. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. These salts and the base compounds can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

Illustrative examples of the compounds of this invention include compounds of Formula I wherein the R groups are designated as follows:

| R | $R^1$ | $R^2$ |
|---|---|---|
| hydrogen | hydrogen | 2-, 3- or 4-pyridinyl |
| ethyl | hydrogen | 2-, 3- or 4-pyridinyl |
| propyl | hydrogen | 5-, 6-, 7- or 8-pyridinyl |
| methyl | benzyl | 2-, 3- or 4-pyridinyl |
| phenethyl | hydrogen | 2-, 3- or 4-pyridinyl |
| phenyl | hydrogen | 2-, 3- or 4-pyridinyl |
| propyl | hydrogen | 2-, 3- or 4-(6, 7-dimethyl)-pyridinyl |
| propyl | hydrogen | 2-, 3-, or 4-(6-phenyl)-pyridinyl |
| 4-methoxyphenethyl | hydrogen | 2, 3- or 4-pyridinyl |
| 4-methoxyphenyl | hydrogen | 2, 3- or 4-pyridinyl |
| benzyl | benzyl | 2-, 3- or 4-(7-ethoxy)-pyridinyl |
| phenyl | phenyl | 2-, 3- or 4-(7-ethoxy)-pyridinyl |
| phenyl | phenyl | 2-, 3- or 4-(7-phenyl)-pyridinyl |
| butyl | hydrogen | 2-, 3- or 4-pyridinyl |
| 3,5-dichloro)-phenylpropyl | methyl | 5-, 6-, 7- or 8-pyridinyl |
| 3,5-dichloro)phenyl | methyl | 5-, 6-, 7- or 8-pyridinyl |
| propyl | methyl | 2-, 3- or 4-pyridinyl |
| 3,5-dimethoxybenzyl | ethyl | 5-, 6-, 7- or 8-pyridinyl |
| 3,5-dimethoxyphenyl | ethyl | 5-, 6-, 7- or 8-pyridinyl |
| methyl | propyl | 2-, 3- or 4-(5-ethoxy-7-methyl)-pyridinyl |
| butyl | butyl | 5-, 6-, 7- or 8-pyridinyl |
| hydrogen | phenethyl | 2-, 3- or 4-(6-trifluoromethyl)-pyridinyl |
| hydrogen | phenethyl | 2-, 3-, or 4-(6-phenyl)-pyridinyl |
| methyl | 4-methoxyphenethyl | 2-, 3- or 4-pyridinyl |

As is true for most classes of therapeutically effective compounds, certain subclasses and certain species which are especially effective are preferred over others. In this instance, those compounds of Formula I where $R_2$ is optionally substituted 2-, 3-, or 4-pyridinyl are preferred. Also preferred are compounds wherein R is $C_1$-$C_6$ alkyl, as well as compounds wherein $R_1$ is hydrogen. Most preferred are the compounds wherein $R_2$ is an unsubstituted 2-, 3-, or 4-pyridinyl group, R is propyl and $R_1$ is hydrogen.

The 2-, 3-, or 4-pyridinyloxazole-2-ones of this invention can readily be prepared by reacting a compound of formula 2

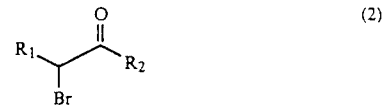

wherein $R_1$ and $R_2$ are as defined above with a cyanate in DMF to form the corresponding isocyanate which undergoes cyclization under the reaction condition to the desired compound.

Another procedure involves cyclizing a hydroxyketone of structure 4

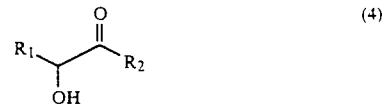

wherein $R_1$ and $R_2$ are as defined above by reaction with a cyanate or salt in the presence of an acid.

The bromo-ketones of formula 2 are either known in the art or can be readily prepared by standard techniques. For example the des-bromo analog of a structure 2 compound can be treated with bromine. Where the group adjacent to the carbon to be brominated is a hydrogen or a ($C_1$-$C_5$) alkyl group, a radical initiator can be used to promote the bromination. Suitable initiators include iron metal and N-bromosuccinimide. The bromination can also be accomplished by the addition of centrated hydrobromic acid, typically 48% aqueous hydrobromic acid, to a solution containing des-bromo compound. The structure (4) hydroxyketones can also be readily prepared in any suitable manner. For example, a structure 2 bromo-ketone can be allowed to react with an acetate salt, preferably potassium acetate, to form the corresponding acetoxyketone which upon treatment with an acid, such as hydrochloric acid, yields the desired structure (4) compound.

The compounds wherein $R_1$ is $C_1$–$C_6$ alkyl or optionally phenyl or substituted $C_1$–$C_3$ alkylphenyl are produced by subsequent reaction of the compound of Formula I wherein $R_1$ is hydrogen with sodium hydride and the appropriate alkyl iodide or phenylalkyl iodide in tetrahydrofuran according to procedures well known in the art.

The ability of the oxazolone derivatives of this invention to act as anti-enveloped virus agents can be demonstrated by their ability to inhibit the growth and replication of murine leukemia virus, an oncogenic retrovirus, as determined by an in vitro XC plaque assay. This assay was performed according to the method of Rowe et al. (*Virology*, 1970, 42, 1136–39) as previously described by L. Hsu, et al. (*J. Virological Methods*, 1980, 1, 167–77) and T. L. Bowlin and M. R. Proffitt (*J. Interferon Res.*, 1983, 3(1), 19–31). Mouse SC-1 cells (fibroblast) ($10^5$) were seeded into each well of 6-well cluster plates (Costar #3506) in 4 ml Minimum Essential Medium (MEM) with 10% Fetal Calf Serum (FCS). Following an 18 hour incubation period (37° C.), Moloney murine leukemia virus (MoLV) was applied at a predetermined titer to give optimal (i.e. countable) numbers of virus plaques. Compounds were added 2 hours prior to addition of the virus. Three days later the culture medium was removed, the SC-1 cell monolayers were exposed to UV irradiation (1800 ergs), and rat XC cells ($10^6$) were seeded into each well in 4 ml MEM. Following an additional 3 day incubation (37° C.), these cells were fixed with ethyl alcohol (95%) and stained with 0.3% crystal violet. Plaques were then counted under low magnification. The antiviral activity of the compound of this invention, 4-propyl-5-(4-pyridinyl)-2(3H)-oxazolone is tabulated in Table 1.

TABLE 1

ANTIRETROVIRAL ACTIVITY OF 4-PROPYL-5-(4-PYRIDINYL)-2(3H)-OXZAOLONE AGAINST MOLONEY MURINE LEUKEMIA VIRUS (MoLv) IN CULTURE

| Compound | Concentration (μg/ml) | Mean No. of Foci | % Inhibition |
| --- | --- | --- | --- |
| Control | | 84 | |
| Test Compound | 1 | 33 | 60.7 |
| Test Compound | 0.75 | 63 | 25 |
| Test Compound | 0.5 | 68 | 19 |
| Test Compound | 0.25 | 67 | 20 |
| Test Compound | 0.10 | 85 | 0 |

The ability of the oxazolone derivatives of this invention to act as anti-enveloped virus agents can be demonstrated by their ability to reduce expression of p24 antigen from HIV infected T-lymphocytes. Cells (C8166 T cell line) were pretreated with test compounds at appropriate concentrations for 3 hours prior to virus (RF strain of HIV-1) absorption. Low multiplicity of infection was used and virus absorption period was 1 hour at room temperature. the cells were washed X1 in PBS and resuspended in fresh medium containing the appropriate concentrations of test compound. Cells incubated at 37° C. and after 3 days culture fluid was assayed for p24 antigen as a measure of viral replication. Because these compounds were tested as the free base, they had to be taken up in DMSO and therefore a series of DMSO virus controls were needed for comparison.

TABLE 2

ANTI-HIV ACTIVITY OF 4-PROPYL-5-(4-PYRIDINYL)-2(3H)OXAZOLONE

| Compound | Concentration (μg/ml) | Vehicle (DMSO) % | p24 Antigen (pg/ml) | % Inhibition |
| --- | --- | --- | --- | --- |
| Vehicle (DMSO) | | 0.1 | 2408 | |
| Control | | 0.1 | 1027 | |
| Test Compound | 10 | 0.1 | 244 | 90 |
| | 1 | 0.01 | 613 | 41 |

The oxazolone derivatives of this invention can be used to treat a number of diseases and conditions known to be caused by enveloped viruses including those diseases and conditions caused by murine leukemia virus, feline leukemia virus, cytomegalovirus (CMV), avian sarcoma virus, herpes simplex virus (HSV), invluenza virus, human immunodeficiency virus (HIV), HTLV-I, and HTLV-II. Those experienced in this field are readily aware of the circumstances requiring anti-enveloped virus therapy. Applicants consider the use of the oxazolone derivatives of this invention to treat HIV infections in humans to be of most importance. The term "patient" used herein is taken to mean mammals such as primates, including humans, sheep, horses, cattle, pigs, dogs, cats, rats and mice.

The amount of the oxazolone derivative of formula 1 to be administered can vary widely according to the particular dosage unit employed, the period of treatment, the age and sex of the patient treated, the nature and extent of the disorder treated, and the particular oxazolone derivative selected. Moreover the oxazolone derivative can be used in conjunction with other agents known to be useful in the treatment of enveloped virus diseases and agents known to be useful to treat the symptoms of and complications associated with diseases and conditions caused by enveloped viruses. The anti-enveloped virally effective amount of a oxazolone derivative of formula 1 to be administered will generally range from about 15 mg/kg to 500 mg/kg. A unit dosage may contain from 25 to 500 mg of the oxazolone derivative, and can be taken one or more times per day. The oxazolone derivative can be administered with a pharmaceutical carrier using conventional dosage unit forms either orally or parenterally.

The preferred route of administration is oral administration. For oral administration the oxazolone derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The oxazolone derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the oxazolone derivative of formula 1 in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol. The following specific examples are presented to illustrate the synthesis of the compounds of this invention, but they should not be construed as limiting the scope of this invention in any way.

The following specific examples are presented to illustrate compositions of this invention, but they should not be construed as limiting the scope of this invention in any way.

EXAMPLE 1

4-Ethyl-5-Pyridin-4-yl-2(3H)-Ozazolone

1-Hydroxy-2-(4-pyridyl)butan-2-one (26.4 g, 0.16 mol) was dissolved in 350 ml of 2N HCl. Potassium cyanate (38.9 g, 0.48 mol) was added portionwise to this solution over a period of one hour with stirring. After the addition was complete, concentrated hydrochloric acid was added until the pH of the solution was one. After an additional hour the reaction mixture was made basic by addition of sodium bicarbonate solution and the resulting mixture was stirred overnight. The resulting solid precipitate was collected and recrystallized twice from 50% aqueous ethanol to yield the title compound (14.4 g, 47% of theoretical yield), m.p. 287°–289° C. (dec.).

Using the procedure above but using 1-(hydroxy)-1-(4-pyridyl)pentan-2-one or 1-(hydroxy)-1-(4-pyridyl)-propan-2-one instead of 1-hydroxy-1-(4-pyridyl)butan-2-one results in 4-propyl-5-pyridin-4-2(3H)-oxazolone, m.p. 257°–259° C. (dec.) or 4-methyl-5-pyridin-4-yl-2(3H)-oxazolone, m.p. >310° C.

EXAMPLE 2

4-Ethyl-5-(2-pyridyl)-2(3H)-oxazolone

Potassium cyanate (35.4 g, 0.44 mol) was added to a solution of 2-hydroxy-1-(2-pyridyl)butan-1-one (31 g, 0.15 mol) in 250 ml of 2N HCl diluted with 300 ml of water. After 1 hour the acidity was adjusted (pH=1) with concentrated hydrochloric acid and then allowed to stir overnight. The mixture was made basic by addition of aqueous sodium bicarbonate. The resulting gummy precipitate was chromatographed on silca gel and recrystallized twice from 50% aqueous ethanol to give the title compound, m.p. 196°–197° C. (dec.).

In a manner substantially similar to that of Examples 1 and 2, the compounds 4-phenyl-5-pyridin-4-yl-2(3H)oxazolone (mp 300° C.) and 4-propyl-5-(2-phenylpyridin-4-yl)-2(3H)-oxazolone (mp 202°–204° C.) were prepared.

EXAMPLE 3

A tablet is prepared from
4-Methyl-5-(3-pyridinyl)-1-(3H)-oxazolone 250 mg
Starch 40 mg
Talc 10 mg
Magnesium 10 mg

EXAMPLE 4

A capsule is prepared from
4-phenyl-5-(2-pyridinyl)-1-(3H)-oxazolone 400 mg
Talc 40 mg
Sodium Carboxymethy celulose 40 mg
Starch 120 mg The compounds of Formula I may also be utilized, in free base form or in compositions, in research and diagnostics, or as analytical references or standards, and the like. Therefore, the present invention includes compositions which are comprised of an inert carrier and an effective amount of a compound of Formula I, or a salt thereof. An inert carrier is any material which does not interreact with the compound to be carried and which lends support, means of conveyance bulk, traceable material, and the like to the compound to be carried. An effective amount of compound is that amount which produces a result or exerts an influence on the particular procedure being performed.

It should be apparent to one of ordinary skill in the art that changes and modifications can be made to this invention without departing from the spirit or scope of the invention as it is set forth herein.

What is claimed is:

1. A method of treating an enveloped viral infection in a patient in need thereof which comprises administering to the patient an anti-enveloped virally effective amount of a compound of the formula

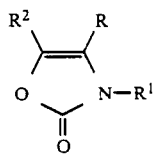 (I)

wherein
R and $R_1$ are each independently selected from the group consisting of hydrogen, $C_1$-$C_6$ alkyl, and phenyl or $C_1$-$C_3$ alkylphenyl wherein the phenyl ring is optionally substituted with one, two or three of the substituents selected from the group consisting of fluorine, chlorine, bromine, $C_1$-$C_4$ alkyl, and $C_1$-$C_4$ alkoxy; and $R_2$ is a 2-, 3-, or 4-pyridyl group wherein the pyridyl group is optionally substituted with one or two substituents selected from the group consisting of fluorine, chlorine, bromine, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, cyano, carboxy, carb($C_1$-$C_5$)alkoxy, carbamido, ($C_1$-$C_5$)alkanoylamino, imidazolyl, nitro and trifluoromethyl or wherein the pyridyl group is optionally substituted with a phenyl group which is optionally substituted with one, two or three of the substituents selected from the group consisting of fluorine, chlorine, bromine, $C_1$-$C_4$ alkyl, and $C_1$-$C_4$ alkoxy; or a pharmaceutically-acceptable salt thereof.

2. A method of claim 1 wherein $R^1$ is a hydrogen.
3. A method of claim 1 wherein R is a methyl, ethyl, or propyl group.
4. A method of claim 1 wherein $R^2$ is 4-pyridinyl, $R_1$ is propyl, and R is hydrogen.
5. A method of claim 1 wherein R is hydrogen, $R^1$ is ethyl and $R^2$ is 4-pyridinyl.
6. A method of claim 1 wherein R is hydrogen, $R^1$ is propyl, and $R^2$ is 4-pyridinyl.
7. A method of claim 1 wherein R is hydrogen, $R^1$ is methyl and $R^2$ is 4-pyridinyl.
8. A method of claim 1 wherein R is hydrogen, $R^1$ is ethyl and $R^2$ is 2-pyridinyl.
9. A method of claim 1 wherein R is hydrogen, $R^1$ is phenyl and $R^2$ is 4-pyridinyl.
10. A method of claim 1 wherein R is hydrogen, R is propyl and $R^2$ is 2-phenylpyridin-4-yl.

* * * * *